(12) United States Patent
Pastorio et al.

(10) Patent No.: US 8,304,559 B2
(45) Date of Patent: Nov. 6, 2012

(54) METHOD FOR THE SYNTHESIS OF 5-AMINO-1-PHENYL-3-CYANO-4-TRIFLUOROMETHYL SULFINYL

(75) Inventors: Andrea Pastorio, Mantova (IT); Paolo Betti, Brescia (IT)

(73) Assignee: Finchimica, S.p.A., Brescia (IT)

( * ) Notice: Subject to any disclaimer, the term of this patent is extended or adjusted under 35 U.S.C. 154(b) by 0 days.

(21) Appl. No.: 13/498,245

(22) PCT Filed: May 26, 2011

(86) PCT No.: PCT/IB2011/052304
§ 371 (c)(1),
(2), (4) Date: Mar. 26, 2012

(87) PCT Pub. No.: WO2012/004692
PCT Pub. Date: Jan. 12, 2012

(65) Prior Publication Data
US 2012/0184753 A1  Jul. 19, 2012

(30) Foreign Application Priority Data
Jul. 7, 2010  (IT) .............................. BS2010A0118

(51) Int. Cl.
*C07D 231/10*  (2006.01)
(52) U.S. Cl. .................................. 548/367.4; 548/373.1
(58) Field of Classification Search ............... 548/367.4, 548/373.1
See application file for complete search history.

(56) References Cited

FOREIGN PATENT DOCUMENTS
WO  WO-01/30760 A1  5/2001
WO  WO-2007/122440 A1  11/2007
WO  WO-2012/007938 A1  1/2012

OTHER PUBLICATIONS
International Search Report and Written Opinion for PCT/IB2011/052304, mailed Sep. 26, 2011; ISA/EP.

*Primary Examiner* — Joseph K. McKane
*Assistant Examiner* — Samantha Shterengarts
(74) *Attorney, Agent, or Firm* — Harness, Dickey & Pierce, PLC

(57) ABSTRACT

The present invention relates to a method for the preparation of the 5-amino-1-phenyl-3-cyano-4-trifluoromethyl sulfinyl pyrazole having the described general formula (I), particularly preferred for the synthesis of Fipronil, through oxidation of a compound having the general formula (II) as follows:

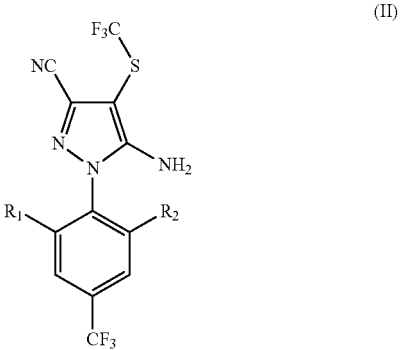

wherein $R_1$ and $R_2$ are independently hydrogen or halogen, and wherein the oxidizing agent is dichloroperacetic acid.

15 Claims, No Drawings

METHOD FOR THE SYNTHESIS OF 5-AMINO-1-PHENYL-3-CYANO-4-TRIFLUOROMETHYL SULFINYL

CROSS-REFERENCE TO RELATED APPLICATIONS

This application is a 371 U.S. National Stage of International Application No. PCT/IB2011/052304, filed May 26, 2011, and claims priority to Italian patent application No. BS2010A000118, filed Jul. 7, 2010, the disclosures of which are herein incorporated by reference in their entirety.

FIELD OF INVENTION

The present invention relates to a method for the synthesis of 5-amino-1-phenyl-3-cyano-4-trifluoromethyl sulfinyl pyrazole having the following general formula (I), particularly preferred for the synthesis of Fipronil.

BACKGROUND OF INVENTION

The synthesis reaction of the compound having the general formula (I):

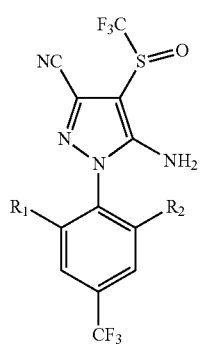

(I)

through oxidation of a compound having the general formula (II) has been described in a variety of documents:

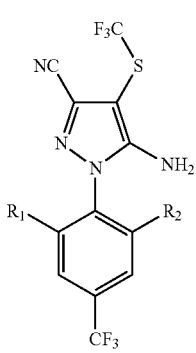

(II)

For example, patent EP 0295117 B1 shows a synthesis method using a 3-chlorobenzoic derivative.

Such synthesis method has evident disadvantages both in terms of yield and of costs, the latter related to the impossibility of re-using the oxidising agent.

A method alternative to the previous one was proposed in document WO 01/030760 A1, where the oxidation step is conducted in the presence of trifluoroperacetic acid (TFPA), obtained from trifluoroacetic acid (TFA) in the presence of hydrogen peroxide and boric acid.

However, also this method is unsatisfactory given the following drawbacks: first of all the trifluoroacetic acid is an extremely expensive reagent which, as a consequence, negatively affects the sales price of the product therewith obtained.

Moreover, during the reaction, hydrogen fluoride is released which eats into the vitreous coatings used in industrial reactors despite operating at temperatures close to ambient temperature. To this purpose, document WO 01/030760 A1 suggests using a corrosion inhibitor which nonetheless entails an additional expense to the overall cost of the process.

Moreover, the use of a corrosion inhibitor would not be adequate to protect all the equipment needed for the recovery process of TFA from the corrosive effect of hydrogen fluoride. The TFA recovery and subsequent reutilisation is a necessary operation dictated by the high cost of TFA compared to common oxidants.

The drawbacks of WO 01/030760 A1 have been overcome thanks to the teaching of document WO 2007/122440 A1 where, instead of TFPA, oxidation is conducted in the presence of trichloroperacetic acid (TCPA).

According to the description, TCPA is the effective oxidising species and is formed in situ by the reaction of an oxidising agent with trichloroacetic acid (TCA).

As well as acting as an oxygen acceptor, TCA should also conveniently act as a reaction solvent.

However, at the temperature at which the reaction takes place, TCA is solid (melting point=54-58° C.) so that, for its use as a reaction solvent, a second solvent needs to be added to the TCA to lower its melting point to a temperature compatible with the reaction temperature.

The solvents suitable for this purpose are, among others, dichloroacetic (DCA) and monochloroacetic (MCA) acids.

In particular, a mixture composed of TCA (70-80%) and DCA (30-20%), characterised by a melting point of 15° C.-30° C., has been shown as suitable for conducting such oxidation reaction where, as mentioned above, the sole purpose of the DCA is to depress TCA's melting point.

However, also this method has the drawback that the oxidant species TCA only allows to operate in a temperature range such as to favour the formation of a by-product having the general formula (III), described below, which has a two-fold disadvantage.

First of all, the reaction forming the by-product consumes useful product to the detriment of the yield.

In addition, the by-product having the general formula (III) is difficult to be separated from the compound having the general formula (I) given its low solubility in common organic solvents thereby requiring an expensive purification process adding to the cost.

A further disadvantageous aspect is that the oxidant species TCA can only be used at temperatures compatible with the oxidation reaction of the compound having the general formula (II) to the compound having the general formula (I) if the reaction is conducted in the presence of a species acting as a solvent both for the reagent having the general formula (II) and for the oxidant TCA itself, making both the recovery operation of the product having the general formula (I) and the recovery of the oxidant TCA more complicated.

In addition, it is realistic to believe that, in the teaching of the prior art document WO 2007/122440 A1, the dichloroacetic acid does not transform into dichloroperacetic acid by means of the hydrogen peroxide or other oxidant, because the species TCA, present in significant molar excess of the oxidant and more reactive towards the oxidants, captures all the available oxygen.

The present invention therefore sets out to provide a new method for the preparation of the compound having the general formula (I) using an economically advantageous oxidation method convenient to implement in industrial applications.

SUMMARY OF INVENTION

The present invention relates to a method for the preparation of the 5-amino-1-phenyl-3-cyano-4-trifluoromethyl sulfinyl pyrazole having the described general formula (I), particularly preferred for the synthesis of Fipronil, through oxidation of a compound having the general formula (II) as follows:

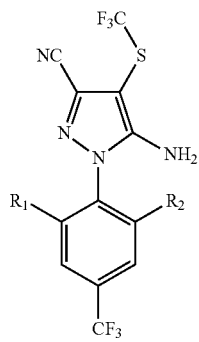

(II)

wherein $R_1$ and $R_2$ are independently hydrogen or halogen, and wherein the oxidising agent can be dichloroperacetic acid.

DETAILED DESCRIPTION

The above objective is achieved by a method for the preparation of the compound having the following general formula (I):

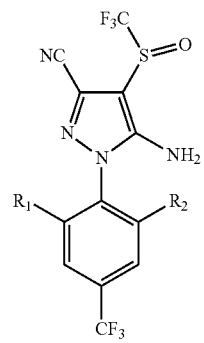

(I)

wherein $R_1$ and $R_2$ are independently hydrogen or halogen; through oxidation of a compound having the general formula (II) in the presence of dichloroacetic acid and of an oxidising agent:

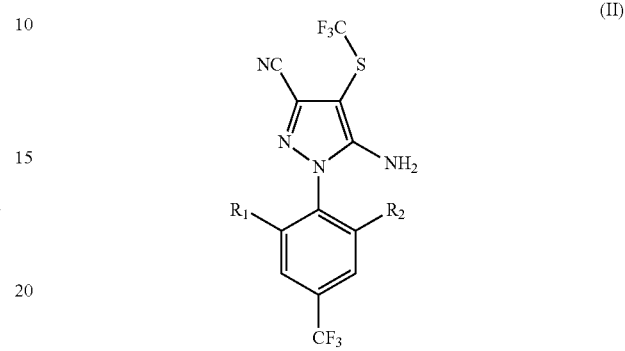

(II)

wherein $R_1$ and $R_2$ are defined as above.

As a result, innovatively, the chemical species causing oxidation of the compound having the general formula (II) to a compound having the general formula (I) is preferably dichloroperacetic acid, formed by oxidation of DCA acid through the oxidising agent.

The use of dichloroperacetic acid as an oxidant has never been described in literature. Surprisingly it was found that DCA, in the presence of an oxidant species such as hydrogen peroxide, peroxide or similar, is also itself transformed at low temperatures into the corresponding dichloroperacetic acid and that this species is an excellent oxidant of the compound having the general formula (II).

In other words, the aforesaid oxidation is conducted in the absence of trichloroacetic and/or trichloroperacetic acid, so that the process of the present invention does not require prior solubilisation of the oxidant.

Preferably, $R_1$ and $R_2$ are chlorine or bromine.

Even more preferably, the compound having the general formula (I) is 5-amino-1-(2,6-dichloro-4-trifluoromethylphenyl)-4-trifluorometansulfinyl-1H-pyrazole-3-carbonitril, commercially known by the name of Fipronil (CAS Registry No. 120068-37-3).

Preferably, the production of the dichloroperacetic acid used in the oxidation of the compound having the general formula (II) is performed in situ, by means of the reaction with the oxidising agent.

As a result, according to such variation, the dichloroacetic acid (DCA) performs, after its partial oxidation in dichloroperacetic acid, the dual function of transferring oxygen to the compound having the general formula (II), and acting as a reaction solvent inasmuch as already liquid at the reaction conditions.

The oxidation of the compound having the general formula (II) to a compound having the general formula (I) is a critical operation, in that the reagent used must be sufficiently energetic to quantitatively conduct such reaction, but without generating the (by-)product of subsequent oxidation having the general formula (III):

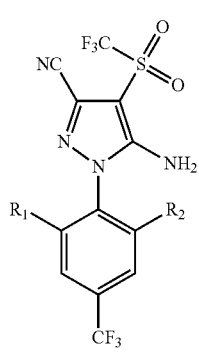

(III)

wherein R₁ and R₂ are again defined as above.

Dichloroperacetic acid proves to be an excellent oxidant for conducting the reaction with good yields and selectivity towards the compound having the general formula (I), without however producing excessive quantities of the undesired product having the general formula (III).

Such good selectivity is not just the result of the intrinsic features of the oxidant species dichloroperacetic acid, but also of the fact that such acid, being liquid, allows to conduct the reaction at a temperature lower than the methods of the prior art, without the use of solvents or melting point depressants.

The present invention therefore allows to operate in the absence of solvents at the same temperatures and to achieve excellent selectivity similar to the ones achieved with trifluoroperacetic acid but without having to use an extremely expensive solvent such as TFA and without having to add corrosion inhibitors which limit, without eliminating, the problem of corrosion of the enamels caused by the hydrogen fluoride generated by such solvent.

According to the present invention, the oxidising agent used is selected from the group comprising benzoyl peroxides, sodium peroxides, t-butyl peroxides and/or hydrogen peroxides.

Among the mentioned oxidising agents, the one that is particularly preferred to oxidise dichloroacetic acid is hydrogen peroxide, in that it can be used in the form of a concentrated aqueous solution.

For example, the concentration of the aqueous solution of hydrogen peroxide is 50%-70% depending on commercial availability, but different concentrations may be just as acceptable.

As regards the precautions suitable for limiting formation of compounds having the aforesaid general formula (III), also the quantity of oxidising agent is a critical variable.

According to an advantageous embodiment, for each mole of compound having the general formula (I), 1.0-5.0 moles of oxidising agent are used, preferably 1.1-2.0 equivalents of such agent, more appropriately 1.5 equivalents for each mole.

In addition, advantageously, for each mole of compound having the general formula (II), 1.5 kg-5 kg of dichloroacetic acid are used.

According to a preferred embodiment variation, the temperature at which oxidation takes place is between 0° C. and 35° C.

Preferably, oxidation takes place at a temperature below 20° C., advantageously at a temperature of 0° C.-15° C., more appropriately at about 5° C.

In fact, as mentioned at the beginning, synthesis methods of the prior art do not enable operation at sufficiently low temperatures to limit the formation of the peroxidation product having the general formula (III), which is generated starting from temperatures near 20° C., in excessive quantities even at low conversion values of the product having the general formula (II).

According to the present invention it is preferable, acting on the reaction time or on the quantity of oxidising agent, to conduct the oxidation reaction up to a conversion level of the compound having the general formula (II) of 80%-98%, preferably 90%-95%.

This way, advantageously, the residual quantity of by-product having the general formula (III) is significantly reduced, and a further, complicated final purification of the product having the general formula (I), entailing inevitable losses in terms of yield and resulting waste production, is made substantially superfluous.

According to one embodiment, the method of the present invention further comprises a step of recovering the non-oxidised compound having the general formula (II).

Preferably, the step of recovering comprises a step of dissolving and subsequently recrystallising the compound having the general formula (I) with one or more of the solvents selected from the group comprising toluene, xylenes, chlorobenzene, chlorinated aliphatic solvents and isopropanol.

According to this embodiment, the unconverted compound having the general formula (II), as a result of its greater solubility than the oxidised forms of formulas (I) and (III) in some organic solvents, can be easily removed by means of a solvent and recovered for re-utilisation as a reagent. This way, during the oxidation process the product loss and the waste production is reduced to a minimum, becoming absolutely negligible.

According to a particularly advantageous embodiment, the oxidation of the compound having the general formula (II) occurs in the presence of an acid catalyst, advantageously homogenous.

This embodiment has proven particularly advantageous, especially in virtue of the large volumes involved in the reaction, to achieve reasonable productivity of the plants.

In fact, the aforesaid oxidation reaction of the compound of general formula (II) is conducted for relatively long periods, with large quantities of solvent to avoid the precipitation of the compounds having the general formula (II) and/or general formula (I), and furthermore at relatively low temperatures, such as below 20° C.

Surprisingly it has been noted that the addition of small quantities of an acid catalyst, in particular sulphuric acid, greatly accelerates the oxidation reaction without any negative effect on selectivity, which in any case remains extremely high.

Preferably, the acid catalyst is a strong mineral acid, advantageously chosen from the group consisting in sulphuric acid, methansulphonic acid, hydrochloric acid, nitric acid and their mixtures.

According to an embodiment, the ratio in moles of the compound having the general formula (II) and the acid catalyst is between 0.3 and 1.5, appropriately between 0.5 and 0.9 and, advantageously, is substantially equal to 0.7.

The purpose of the present invention will now be illustrated on the basis of several, non-limiting examples.

EXAMPLE 1

Synthesis of Fipronil

In a glass reactor, 421 grams (1.0 moles) of 5-amino-1-(2, 6-dichloro-4-trifluoromethyl-phenyl)-4-trifluorometan-sulfanil-1H-pyrazole-3-carbonitrile hereafter "sulphide") are dissolved in 2300 grams of dichloroacetic acid (DCA). The solution obtained is stirred and kept at 20° C. after which 102 grams of hydrogen peroxide in an aqueous solution 50% w/w (1.5 moles) are added.

The reaction is monitored using HPLC analysis until it reaches a conversion level of more than 95% of the reagent sulphide, after which the reaction mixture is diluted with 4 liters of water until the product has precipitated entirely.

The solid thus obtained is filtered, washed with water and dried to obtain 420 grams of product with a purity of 93.5%.

EXAMPLE 2

Synthesis of Fipronil with Subsequent Recovery of Unconverted Reagent Compound Having the General Formula (II)

In a glass reactor 421 grams (1.0 mole) of 5-amino-1-(2, 6-dichloro-4-trifluoromethyl-phenyl)-4-trifluorometan-sulfanil-1H-pyrazole-3-carbonitrile (hereafter "sulphide") are dissolved in 2300 grams of dichloroacetic acid (DCA). The solution obtained is stirred and kept at 20° C., after which 102 grams of hydrogen peroxide in an aqueous solution 50% w/w (1.5 moles) are added.

The reaction is monitored using HPLC analysis until it reaches a conversion level of 92% of the reagent sulphide, so as to limit the formation of the by-product (III) difficult to remove by means of re-crystallisation. When the desired conversion level has been reached the reaction mixture is diluted with 4 liters of water until the product has precipitated entirely.

The solid thus obtained is filtered, washed with water and dried.

After drying the raw product is dissolved while hot in chlorobenzene solvent and re-crystallised by cooling to a low temperature. The solid thus obtained is composed of Fipronil with a purity of over 95%.

The filtrate, containing only sulphide and small quantities of Fipronil, is deprived of the solvent chlorobenzene and added as a reagent to a subsequent oxidation reaction.

EXAMPLE 3

Synthesis of Fipronil with Addition of Sulphuric Acid and Comparison With Example 1 and with WO 2007/122440 A1

In a glass reactor 421 grams (1.0 mole) of 5-amino-1-(2, 6-dichloro-4-trifluoromethyl-phenyl)-4-trifluorometan-sulfanil-1H-pyrazole-3-carbonitrile (hereafter "sulphide") are dissolved in 2300 grams of dichloroacetic acid (DCA). The solution obtained is stirred and kept at 20° C. and subsequently 102 grams of hydrogen peroxide in aqueous solution 50% w/w (1.5 moles) and 70 grams (0.7 moles) of $H_2SO_4$ are added.

The reaction is conducted at a temperature of 5 to 10° C. and monitored by means of HPLC analysis until it reaches a conversion level of over 95% of the reagent sulphide, after which the reaction mixture is diluted with 4 liters of water until the product has precipitated entirely.

The solid thus obtained is filtered, washed with water and dried to obtain 420 grams of a product with a titre of 93.5%.

According to this example, the desired conversion level is reached in about 3 hours compared to the 20 hours of the previous example 1. The reaction conducted at 20° C. according to the examples shown in the earlier document WO 2007/122440 A1, mentioned at the beginning, lasts about 8 hours.

Innovatively, the method of the present invention is conducted in the presence of an oxidising agent and of dichloroacetic acid making a plurality of operations superfluous, for example dissolution, otherwise essential in the known methods.

Advantageously, the method of the present invention allows to achieve higher yields compared to the methods of the prior art, in that the reaction takes place with improved selectivity thereby preventing the consumption of useful product in parasite reactions.

Advantageously, the method of the present invention, once the excess of unconverted reagent (II) has been easily recovered, makes subsequent purification of the compound having the general formula (I) superfluous, which as well as being burdensome in itself is economically disadvantageous.

Advantageously, the use of the oxidising agent of the present invention does not require the use of solvents for the reaction, making the entire process much simpler and economically advantageous in industrial applications.

In fact, according to a further advantageous aspect, the cost of such oxidant is lower than the cost of the oxidants traditionally used.

Advantageously, the function performed by the DCA in the method of the present invention enables economies in terms of costs of the reagents, and simplification of the plant for implementing the teaching.

Advantageously, the process of the present invention makes the use of corrosion inhibitors superfluous and allows to drastically increase the useful life of the equipment used.

It was, in fact, observation of the premature corrosion of the plants which urged the authors of the present invention to look for an oxidant agent alternative to the oxidants traditionally used.

As a result, the aforesaid advantage is twofold in that it derives both from the non-use of a corrosion inhibitor and from the increased useful life of the equipment.

Advantageously, the addition of an acid catalyst makes it possible to considerably reduce reaction times while maintaining a high degree of selectivity of oxidation of the compound having the general formula (II).

Even if not previously specified, a person skilled in the art may, using the expertise typical of the sector, vary or replace some of the aspects described above with other technically equivalent ones.

For example, dichloroperacetic acid may be prepared separately from the place where oxidation of the compound having the general formula (II) takes place, for subsequent addition to the latter.

Moreover, one embodiment envisages that the peroxides illustrated earlier may be replaced or used in conjunction with a peracid and/or a persulphate.

These variations or replacements also fall within the scope of protection defined by the following claims.

In addition, any alternative shown in relation to a particular embodiment may be realised independently of the other variations described.

The invention claimed is:

1. A method for the preparation of the compound having the following general formula (I):

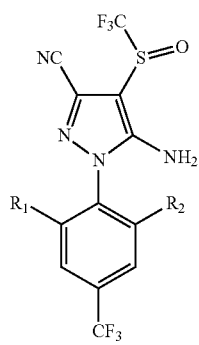

(I)

wherein $R_1$ and $R_2$ are independently hydrogen or halogen; through oxidation of a compound having the general formula (II) in the presence of dichloroacetic acid and of an oxidising agent:

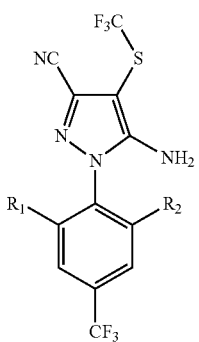

(II)

wherein $R_1$ and $R_2$ are defined as above, where the oxidising agent is selected from the group comprising benzoyl peroxides, sodium peroxides, t-butyl peroxides and/or hydrogen peroxide, and wherein the oxidation is conducted in the absence of trichloroacetic and/or trichloroperacetic acid.

2. The method according to claim 1, wherein $R_1$ and $R_2$ are chlorine or bromine.

3. The method according to claim 1, wherein the compound having the general formula (I) is 5-amino-1-(2,6-dichloro-4-trifluoromethyl-phenyl)-4-trifluorometansulfinyl-1H-pyrazole-3-carbonitrile.

4. The method according to claim 1, wherein the dichloroacetic acid is oxidised to dichloroperacetic acid through the oxidising agent.

5. The method according to claim 4, wherein oxidation of the dichloroacetic acid takes place in situ.

6. The method according to claim 1, wherein, for each mole of compound having the general formula (I), 1.0-5.0 moles of oxidising agent are used.

7. The method according to claim 1, wherein, for each mole of compound having the general formula (I), 1.1-2.0 equivalents of oxidising agent are used.

8. The method according to claim 1, wherein, for each mole of compound having the general formula (II), 1.5 kg to 5 kg of dichloroacetic acid are used.

9. The method according to claim 1, wherein the temperature at which oxidation takes place is between 0° C. and 35° C.

10. The method according claim 1, wherein the temperature at which oxidation takes place is between 0° C.-20° C. and, preferably is 5° C.

11. The method according to claim 1, further comprising a step of recovering the non-oxidised compound having the general formula (II).

12. The method according to claim 11, wherein the step of recovering comprises a step of dissolving and subsequently recrystallising the compound having the general formula (I) with one or more of the solvents selected from the group comprising toluene, xylene, chlorobenzene, chlorinated aliphatic solvents and isopropanol.

13. The method according to claim 1, wherein the oxidation of the compound having the general formula (II) occurs in the presence of an acid catalyst.

14. The method according to claim 13, wherein the acid catalyst is a strong mineral acid selected from the group consisting in sulphuric acid, methanesulphonic acid, hydrochloric acid, nitric acid and their mixtures.

15. The method according to claim 13, wherein the ratio in moles between the compound of general formula (II) and the acid catalyst is 0.3 to 1.5, and is preferably substantially equal to 0.7.

* * * * *